United States Patent
Ohtaka et al.

(10) Patent No.: US 7,427,761 B2
(45) Date of Patent: Sep. 23, 2008

(54) VISUALIZING APPARATUS USING GAMMA RAY SOURCE

(75) Inventors: Masahiko Ohtaka, Higashi-Ibaraki-gun (JP); Kuniaki Ara, Higashi-Ibaraki-gun (JP); Hitoshi Hayashida, Higashi-Ibaraki-gun (JP); Masaru Hirabayashi, Higashi-Ibaraki-gun (JP)

(73) Assignee: Japan Atomic Energy Agency, Ibaraki-ken (JP)

( * ) Notice: Subject to any disclaimer, the term of this patent is extended or adjusted under 35 U.S.C. 154(b) by 296 days.

(21) Appl. No.: 11/384,378

(22) Filed: Mar. 21, 2006

(65) Prior Publication Data

US 2007/0069147 A1 Mar. 29, 2007

(30) Foreign Application Priority Data

Sep. 29, 2005 (JP) ............................. 2005-285073

(51) Int. Cl.
*G01J 1/42* (2006.01)
(52) U.S. Cl. ...................................... 250/393
(58) Field of Classification Search ................. 250/393
See application file for complete search history.

(56) References Cited

U.S. PATENT DOCUMENTS 3,878,373 A * 4/1975 Blum .......................... 250/303

6,792,069 B2 9/2004 Hirabayashi et al.

FOREIGN PATENT DOCUMENTS

JP 2003-194740 7/2003

* cited by examiner

*Primary Examiner*—David P. Porta
*Assistant Examiner*—Kiho Kim
(74) *Attorney, Agent, or Firm*—Wenderoth, Lind & Ponack, L.L.P.

(57) ABSTRACT

Discriminating radioactive nuclides of a gamma ray source and nondestructively measuring an image concentration and spatial distribution of a gamma ray by radioactive nuclides. A visualizing apparatus having a container 1 including a gamma ray source 2; a gamma ray detector 7 around the container 1 which detects gamma rays through a collimator 6; a gamma ray detection signal processing device 9 which processes a gamma ray detection signal measuring energy and counted value thereof; an energy discrimination processing device 10 which performs discrimination and intensity analysis of radioactive nuclides by performing spectrum analysis of gamma ray energy and intensity measured for each unit time or position; an imaging calculation processing device 11 which forms images of concentration and space distribution of the gamma ray source for each discriminated radioactive nuclide; and an image display device 12 which performs visual display based on a result of the calculation processing.

4 Claims, 8 Drawing Sheets

Measurement object (structure in liquid metal (Na))

Visualization example by numerical simulation

Verification example by numerical simulation
(Visualization example of radiation source in copper container and portion other than radiation source)

Measurement object (uranium in metal container)

- Storage container (casing)
- 2 Uranium
- 1 Metal container

Visualization example by numerical simulation

Distributed uranium concentration

VISUALIZING APPARATUS USING GAMMA RAY SOURCE

BACKGROUND OF THE INVENTION

1. Field of the Invention

The present invention relates to an apparatus which visualizes an object to be measured (a measurement object) by utilizing a gamma ray source included in the measurement object. This technique is useful for visualizing a gamma ray source in a radioactive isotope handling apparatus and facility in the field of the nuclear fuel cycle (for example, enrichment, reprocessing, waste management/processing/disposal of nuclear fuel), and the like.

2. Description of the Related Art

There is an industrial X-ray CT scanner as an inspection apparatus which performs the imaging of the inside of a measurement object. The industrial X-ray CT scanner adopts a system in which an X-ray source outside the measurement object is needed to irradiate X-rays to the measurement object, so that a large-scale X-ray generator using a linear accelerator and the like is used. Therefore, an auxiliary apparatus such as an energy supply apparatus is needed for generating X-rays, as a result of which the industrial X-ray CT scanner as a whole is inevitably enlarged. Further, since the generation direction of X-rays and the X-ray detector need to be precisely positioned, the industrial X-ray CT scanner is assumed to be fixed and used. This leads to a restriction that the measurement object must be arranged so as to be movable. Further, the industrial X-ray CT scanner is constituted as a large-sized permanent facility, so that its maintenance is difficult to be performed.

As a technique which is capable of solving the above described problems, there is proposed an apparatus in which a radiation source is inserted in a heat exchanger tube to be inspected, and is utilized to image the cross section of the heat exchanger tube, so as to make it possible to easily and nondestructively perform inspection of defects and wall thickness of the tube, and the like (see Japanese Patent Laid-Open No. 2003-194740). However, this prior art is intended to perform the inspection of defects of the heat exchanger tube to be inspected itself, so that the cross section of the heat exchanger tube is imaged only by detecting the presence or absence of radiation. In this case, the radiation source is known and is inserted at the time of inspection, and hence, an operation such as to specify a nuclide is not needed. In such a technique, the analysis including specifying a radioactive nuclide cannot be effected, and need not be effected. Therefore, in this technique, it is impossible to discriminate a ray source nuclide and to measure concentration and spatial distribution of the ray source nuclide in the measurement object including a radiation source.

SUMMARY OF THE INVENTION

An object of the present invention is to enable a radioactive nuclide of a gamma ray source included in a measurement object such as an apparatus, to be discriminated, and to enable concentration and spatial distribution of gamma rays emitted from each radioactive nuclide to be nondestructively measured and imaged.

According to the present invention, there is provided a visualizing apparatus utilizing a gamma ray source comprising: a collimator which is arranged around a measurement object including the gamma ray source, and which allows gamma rays in a specific incoming direction from the gamma ray source to pass through; a gamma ray detector which detects the gamma rays passing through the collimator; a gamma ray detection signal processing device which processes a gamma ray detection signal detected by the gamma ray detector to measure energy and counted value of the detection signal; an energy discrimination processing device which performs discrimination and intensity analysis of radioactive nuclides by performing spectrum analysis of the gamma ray energy and the gamma ray intensity measured for each unit time or unit position; an imaging calculation processing device which forms images of the concentration and space distribution of the gamma ray source in the measurement object for each discriminated radioactive nuclide; and an image display device which performs visual display on the basis of the result of the calculation processing.

Here, it is preferred that the measurement object including the gamma ray source and the gamma ray detector provided with the collimator perform a relative rotational movement or a relative linear movement, that the energy discrimination processing device performs discrimination and intensity analysis of radioactive nuclides by taking into account position and time signals of the relative rotational movement or the relative linear movement, and that the imaging calculation processing device forms an image as an aggregate of discrete pixels by performing repetitive calculation of pixel values showing the gamma ray intensity.

The visualizing apparatus according to the present invention is constituted so as to measure gamma rays emitted from the gamma ray source included in the measurement object, to perform discrimination and intensity analysis of radioactive nuclides by performing spectrum analysis of gamma ray energy and gamma ray intensity which are measured for each unit time or unit position, and to form images of concentration and spatial distribution of the gamma ray source included in the measurement object for each discriminated radioactive nuclide. Thereby, it is possible to discriminate the ray source nuclides, to confirm the concentration and spatial distribution of the gamma rays as images, and to visually display the resultant area where the ray source is not present, as a result of which the shape and state of the structure inside the measurement object can also be monitored. Further, even in the case where the measurement object is a rotating body or a moving body, the visualizing apparatus according to the present invention can perform the measurement by making the gamma ray detector synchronized to the rotation or the movement of the measurement object.

Further, in the case where the gamma rays are measured by moving the gamma ray source, the visualizing apparatus according to the present invention can perform the visualization even by one directional measurement, and hence can also be utilized in a narrow place. In this case, since neither the collimator nor the gamma ray detector needs to be moved, a track and control device for the movement are not needed, so that miniaturization and cost reduction of the apparatus can be achieved. In addition, a cause of image quality degradation due to the movement can also be eliminated so that high image quality can be realized.

BRIEF DESCRIPTION OF THE DRAWINGS

FIGS. 3A, 3B and 3C are illustrations showing a first verification example by a numerical simulation based on the image calculation processing, wherein FIG. 3A shows a model of the measurement object, and FIGS. 3B and 3C show the result of the processing;

FIGS. 4A and 4B are illustrations showing a second verification example by the numerical simulation based on the image calculation processing, wherein FIG. 4A shows a model of the measurement object, and FIG. 4B shows the result of the processing;

DETAILED DESCRIPTION OF THE PREFERRED EMBODIMENTS

Figure 1A:
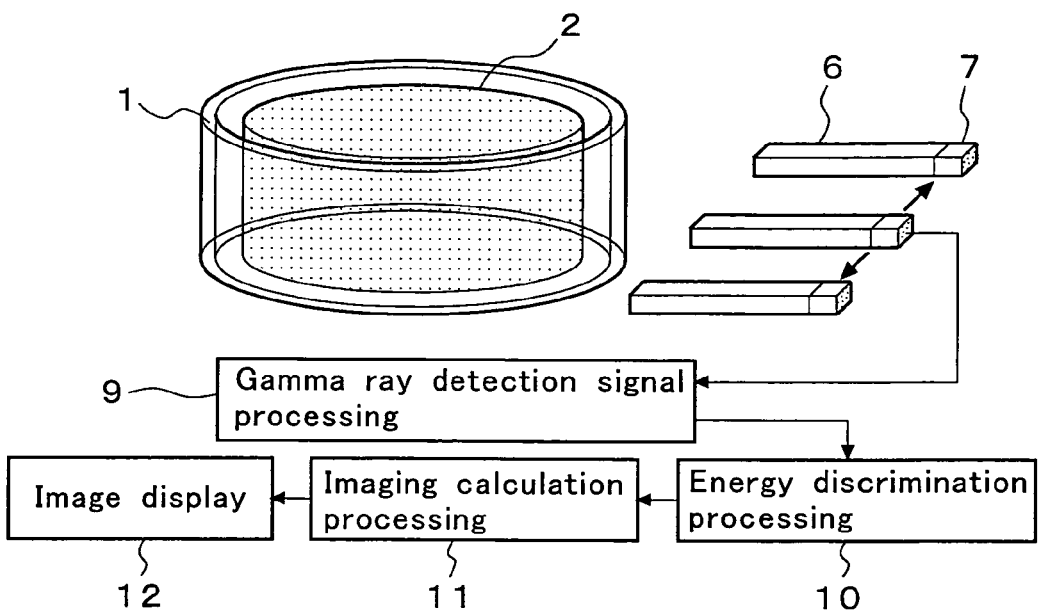
FIG. 1A is an illustration showing a fundamental configuration and operation of a visualizing apparatus according to the present invention.
Figure 1B:
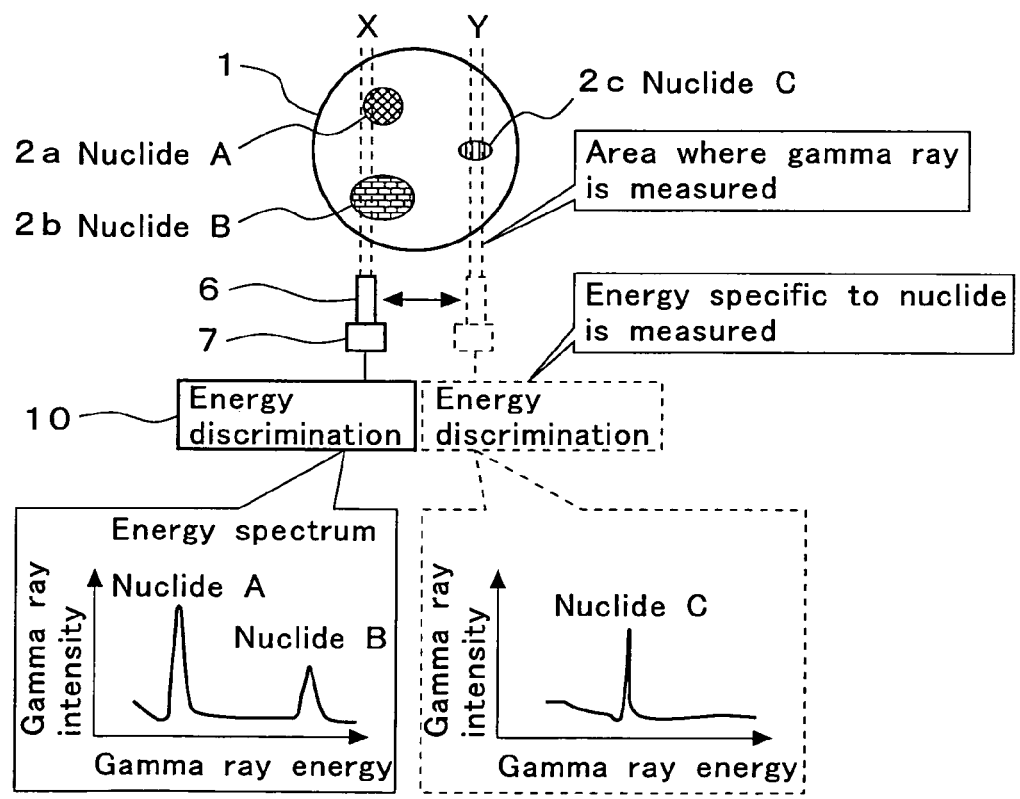
FIG. 1B is an illustration showing energy discrimination processing.

FIGS. 1A and 1B show a fundamental configuration and operation of a visualizing apparatus utilizing a gamma ray source, according to the present invention. Here, as a measurement object, there is shown an example in which the gamma ray source 2 is enclosed in a cylindrical container 1, but the shape, material and the like of the container may be arbitrary. Around the measurement object, there are arranged a collimator 6 and a gamma ray detector 7, by which the incoming direction and the energy of gamma rays are made to be detected. Further, the output of the gamma ray detector 7 is arranged to be processed by a gamma ray detection signal processing device 9, an energy discrimination processing device 10, and an imaging calculation processing device 11, and then to be displayed by an image display device 12. Noted that for simplicity of the present description, similar members, devices and the like in each of the following figures are denoted by the same reference numerals.

The collimator 6 and the gamma ray detector 7 are arranged around the container 1 in which the gamma ray source 2 is enclosed. Gamma rays emitted from the gamma ray source 2 are transmitted to the outside of the container 1. The gamma rays are isotropically emitted from the inside of the container 1, but only the gamma rays of a certain incoming direction are made incident on the gamma ray detector 7 by the collimator 6. The energy and counted value of the gamma rays made incident on the gamma ray detector 7 are measured by the gamma ray detection signal processing device 9. The measured signal is discriminated by the energy discrimination processing device 10 in accordance with the energy of the signal, and is recorded together with the counted value.

Here, the gamma ray detector 7 is rotated or moved, or the plurality of gamma ray detectors 7 are used, or the measurement object is moved, so that the data of energy intensity of gamma rays are measured from various directions with respect to the gamma ray source 2 enclosed in the container 1, and collected. Alternatively, instead of moving or rotating the gamma ray detector 7, the measurement object may be moved or rotated. In the individual measured data, the counted value changes in accordance with the abundance rate of gamma rays and the gamma ray absorptance depending upon the material density, and hence, the place where the gamma rays are present and where the material is present can be reproduced as an image by performing the measurement from various directions.

First, the energy discrimination processing and the imaging calculation processing which constitute the main portion of the present invention are described. The contents of the energy discrimination processing are shown in FIG. 1B. However, for the sake of clarity of the description, here, the gamma ray source is described as consisting of three kinds of gamma ray sources (nuclide A, nuclide B, nuclide C), unlike the gamma ray source shown in FIG. 1A. When the collimator 6 and the gamma ray detector 7 are in the position X, gamma rays emitted from the nuclide A and the nuclide B, which are present in the gamma ray measurable area at the position X (the area shown between the broken lines in FIG. 1B), are incident on the gamma ray detector 7. Further, when the collimator 6 and the gamma ray detector 7 reach the position Y, gamma rays emitted from the nuclide C, which is present in the gamma ray measurable area at the position Y, is incident on the gamma ray detector 7. In this way, the gamma rays are incident on the gamma ray detector 7 for each minute moving time period or each minute position movement in accordance with the movement of the collimator 6 and the gamma ray detector 7. The gamma rays incident on the gamma ray detector 7 are subjected to the energy discrimination processing for each unit time or each unit position.

In the energy discrimination processing, an energy spectrum between the gamma ray energy and the gamma ray intensity for each unit time or each unit position, is formed as shown in the lower part of FIG. 1B. In this stage, by analyzing the peak of gamma ray intensity for each gamma ray energy in the energy spectrum, it is possible to specify the gamma ray sources (nuclide A, nuclide B, nuclide C). The analyzed data are used as data for the subsequent analysis to be performed by the imaging calculation processing device 11.

Figure 2:
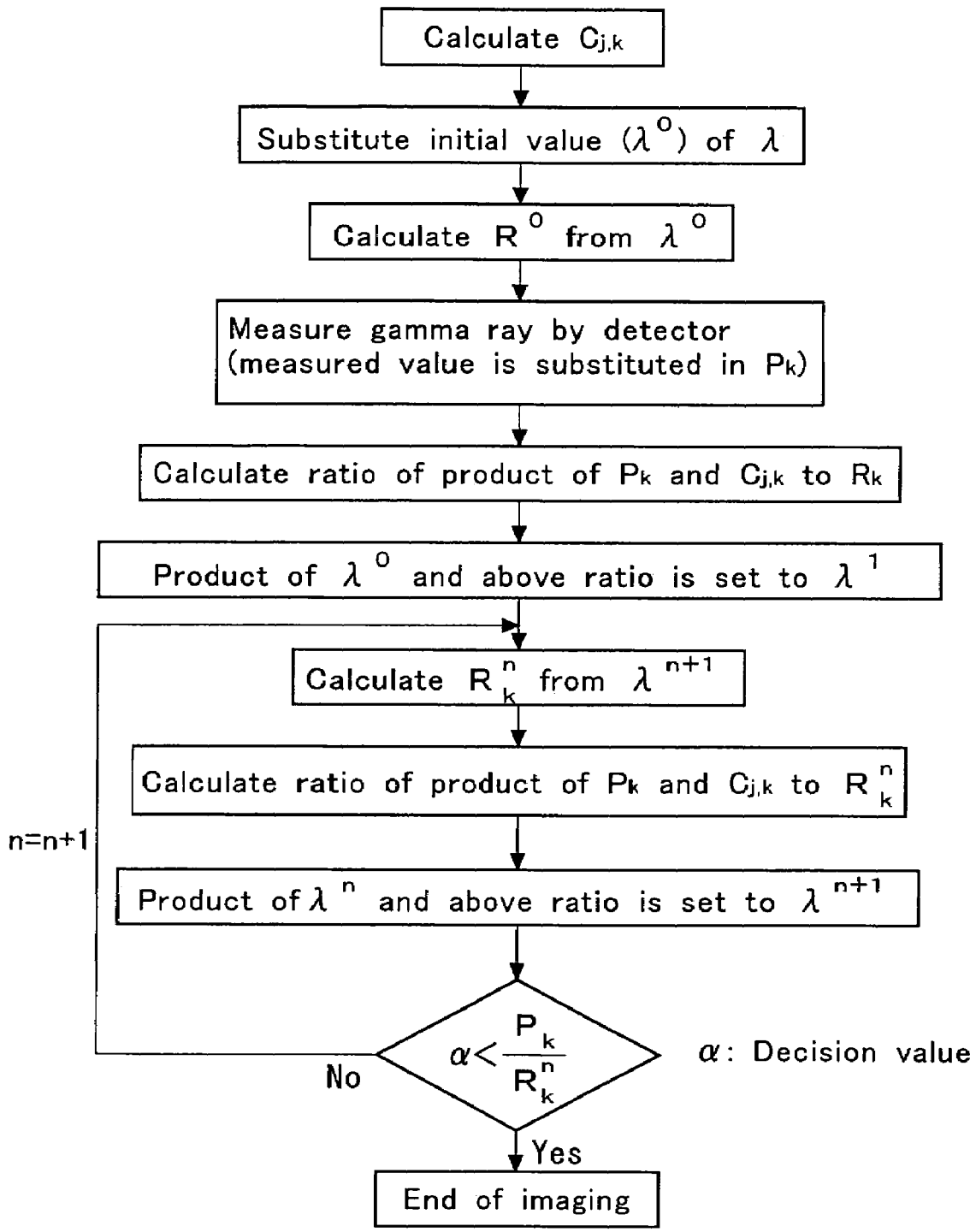
FIG. 2 is a flow chart of image calculation processing.

Next, a description is given of imaging. The imaging processing is performed by making the data analyzed by the energy discrimination processing device 10 synchronous in phase to the position of the nuclides and the moving position of the gamma ray detector 7 and the like, for each radioactive nuclide. Specifically, repetitive calculation is performed by using the following formula (1), so that the analyzed data can be imaged as an aggregate of discrete pixels. After the imaging calculation processing is performed by using the formula (1), the gamma ray sources themselves can be visualized by the image display device 12. FIG. 2 shows a flow chart of the imaging calculation processing.

$$\lambda_j^{n+1} = \lambda_j^n \frac{\sum_{k=1}^{K} \frac{P_k^{n+1} \cdot c_{j,k}}{R_k^n}}{\sum_{k=1}^{K} c_{j,k}}$$ [Formula 1]

$\lambda_j$: j-th pixel value=gamma ray intensity $P_k$: gamma ray energy and intensity data measured by the k-th gamma ray detector $R_k$: data of gamma rays incident on the k-th detector based on the pixel value $\lambda^n_j$ after the n-th repetitive calculation k: serial number indicating the position of the gamma ray detector (total K in the case of T directions)

j: the j-th pixel n: repeat count $C_{j,k}$: probability that gamma rays emitted from the pixel j are detected at the k-th detector position (contribution rate to the pixel)

Figure 3A:
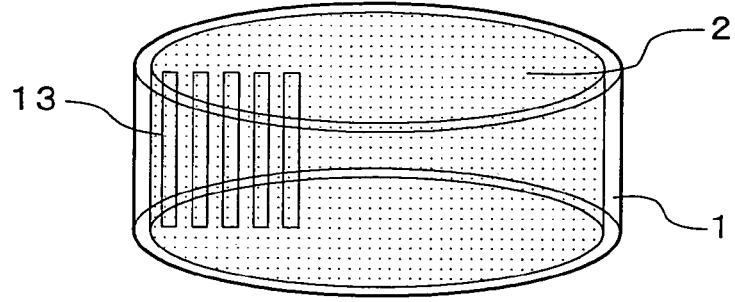
Figure 3B:
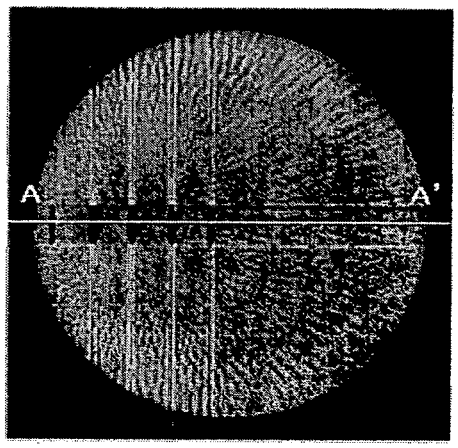
Figure 3C:
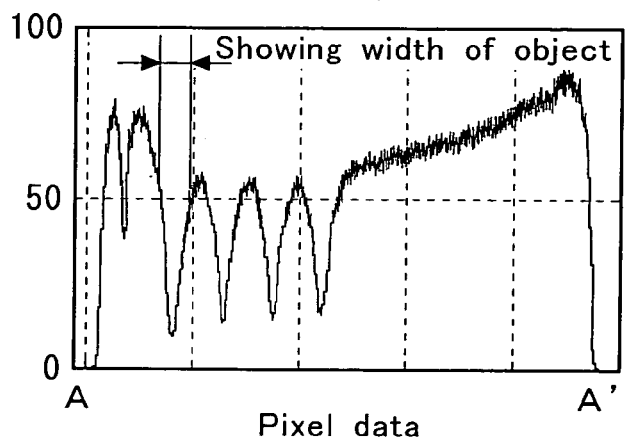

FIGS. 3A, 3B and 3C show a first verification example by a numerical simulation. FIG. 3A shows a model of a measurement object. As for the measurement object, a case is assumed where a gamma ray source 2 made of a liquid metal is uniformly distributed in a container 1 having a diameter of about 1 m (a metallic cylindrical shape and a wall thickness of 15 mm), in which a plurality of metal plates 13 (having a thickness of 10 mm) are present. The energy of gamma ray is assumed to be 2.75 MeV corresponding to the energy of gamma ray emitted from Na-24. On the basis of this assumption, the gamma ray measured by a collimator 6 and a gamma ray detector 7 at the outer circumference of the container 1 is simulated, and the imaging calculation processing is performed by using the data obtained by the simulation. FIG. 3B shows the result of the processing. The radiation source area is visualized in a circular form which is the shape of the container 1, while the metal plates 13 which are present in the optically opaque liquid metal are also visualized. Further, as shown in FIG. 3C, the quantitative information (presence position and the like) relating to the shape can also be obtained by analyzing pixel data along line A-A' in FIG. 3B.

As a result of the numerical simulation, it is clearly shown that the radiation source area is visualized, and at the same time, the container 1 including the radiation source and the metal plates 13 are also visualized as the regions where the radiation source is not present. Therefore, it is obvious that the numerical simulation can be employed in the application for contactlessly confirming a distribution state of a radiation source, a shape of a container which includes the radiation source, a state of inner structures of an apparatus including the radiation source, and the like.

Figure 4A:
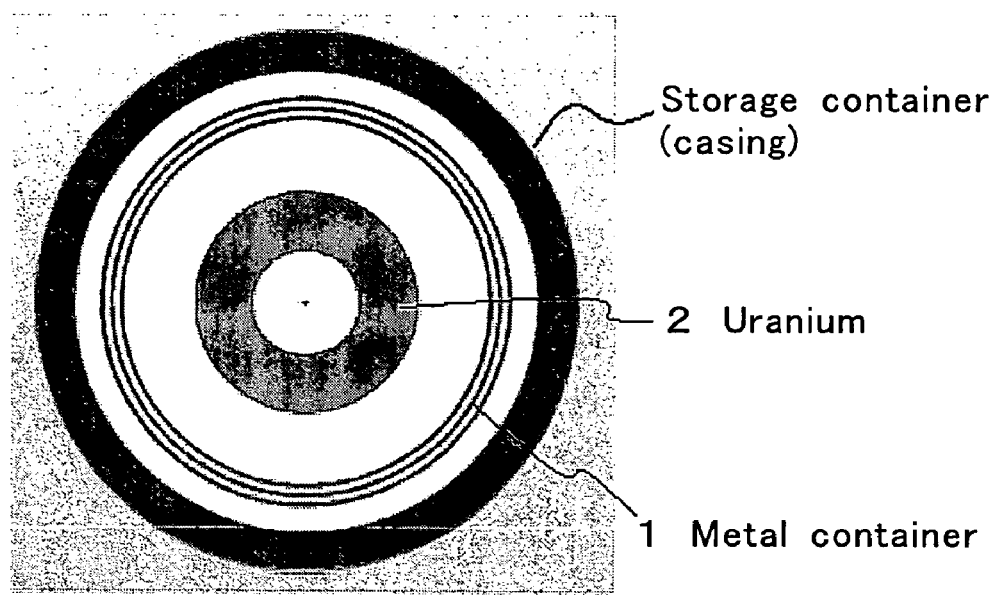
Figure 4B:
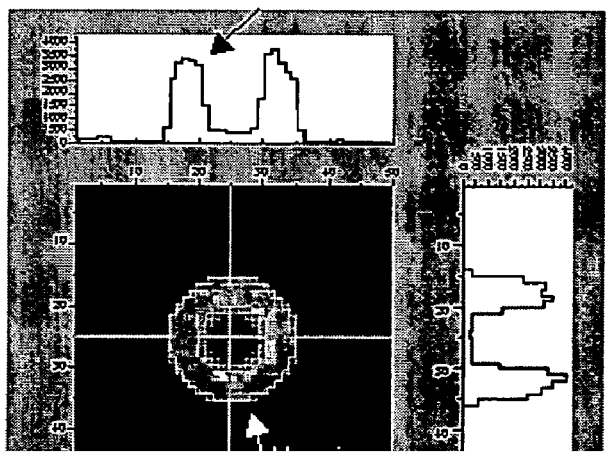

FIGS. 4A and 4B show a second verification example by the numerical simulation. FIG. 4A shows a model of the measurement object. As for the measurement object, it is assumed that uranium is distributed in a doughnut shape in a container 1 having a plurality of layers (metallic container having a thin wall thickness of about 1 mm), the container being provided in a metallic storage container (casing) having a wall thickness of about 20 mm. The energy of gamma ray is assumed to be 186 KeV corresponding to the energy of gamma ray emitted from U-235. On the basis of this assumption, the gamma ray measured by a collimator 6 and a gamma ray detector 7 at the outer circumference of the container 1 is simulated, and the imaging processing is performed by using the data obtained by the simulation. FIG. 4B shows the result of the processing. The position and concentration of the uranium are visualized as a doughnut-shaped distribution state. At the same time, the result shows that the visualization can also be effected in the gamma ray energy different from that of the first verification example based on the numerical simulation. It is seen from the above result that discrimination of nuclides (the nuclide is uranium in this case) can also be effected.

Embodiment

Figure 5:
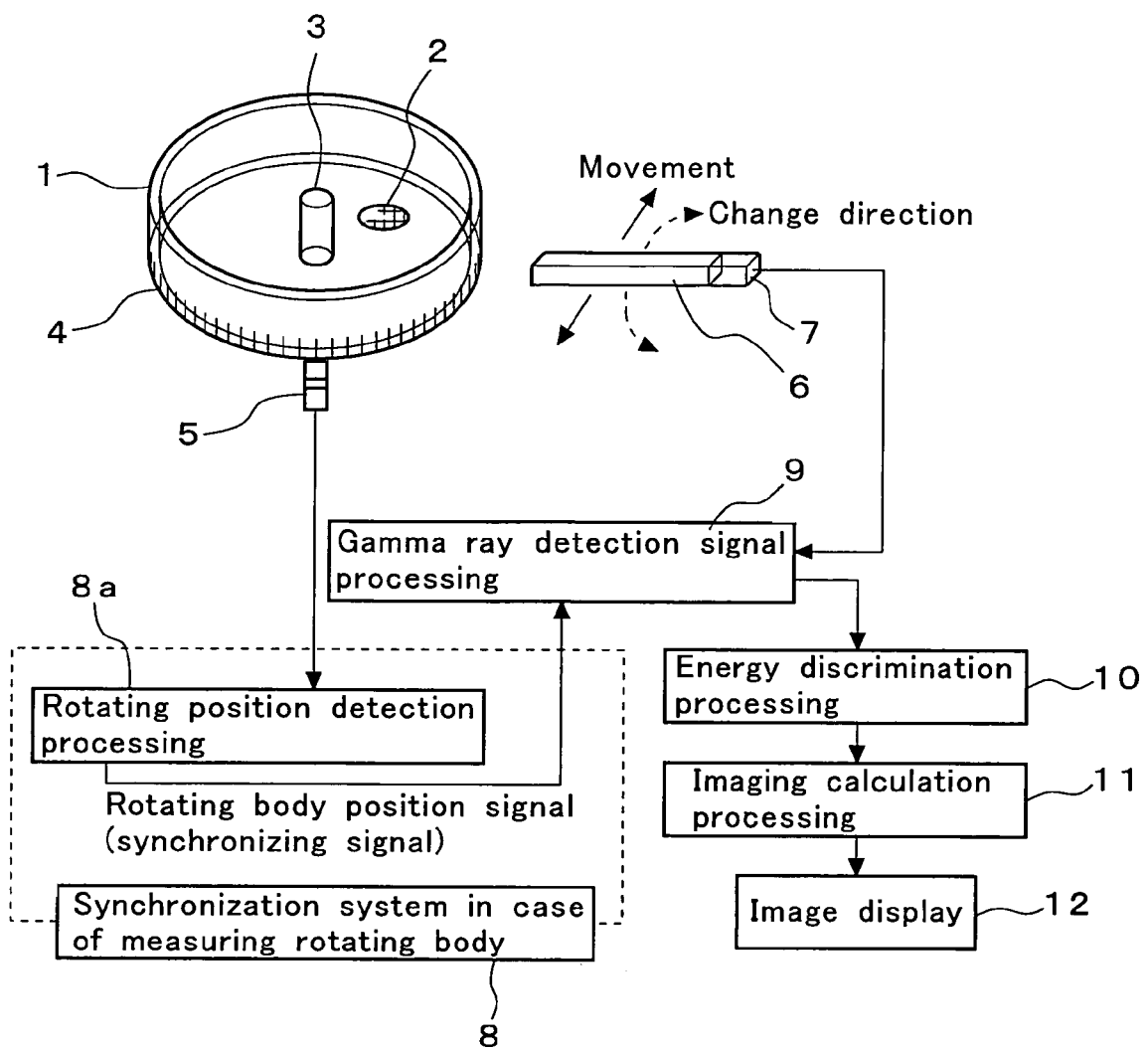
FIG. 5 is an illustration showing an embodiment of the visualizing apparatus according to the present invention.

FIG. 5 is an illustration showing an embodiment of a visualizing apparatus utilizing a gamma ray source, according to the present invention, and showing an example of visualization of the gamma ray source provided in a rotating body. A gamma ray source 2 is present in a container 1 and arranged to be rotatable about a rotating shaft 3. Here, the container 1 is formed to be cylindrical, but the shape and material of the container is not specifically restricted. A rotational position detection marker 4 is provided for the outer circumference of the container 1. The marker is formed of a paint, a magnetic material, protruded/recessed parts or the like, and may be an object which can be detected by optical, magnetic or contact-type sensors. In this example, the markers are provided at a plurality of spots at equal intervals, but the marker may be provided at least one spot. A rotational position detecting sensor 5 for detecting the rotational position of the container 1 is provided outside of the container 1. The rotational position detecting sensor 5 may be of any type including the optical type, the magnetic type, the contact-type and the like, provided that the sensor is capable of responding to the rotational position detection marker 4 and detecting the marker.

Around the container 1, there are arranged a collimator 6 and a gamma ray detector 7, by which the incoming direction and the energy of gamma rays can be detected. The gamma rays emitted from the gamma ray source 2 are isotropically emitted and transmitted to the outside of the container 1, but the gamma rays in a certain incoming direction are made incident on the gamma ray detector 7 by the collimator 6.

In this embodiment, a synchronization system 8 in the case of measuring the rotating body is additionally provided. Specifically, a rotational position detection processing device 8a is provided, which measures the rotational position of the container 1 from the signal of the rotational position detecting sensor 5, and which outputs a synchronizing signal for signal reception by the gamma ray detector 7. A gamma ray detection signal processing device 9 receives gamma ray measurement data in a timing based on the synchronizing signal outputted from the rotational position detection processing device 8a. That is, the energy and counted value of the gamma rays incident on the gamma ray detector 7 are measured in the gamma ray detection signal processing device 9, at the time when the synchronizing signal outputted from the rotational position detection processing device 8a is inputted, or at the time of the end of a set time period after the synchronizing signal is inputted.

The measured signal is discriminated by the energy discrimination processing device 10 in accordance with the energy, and is recorded together with the counted value. After the energy and intensity of gamma rays which are gamma ray data are measured at a number of rotational positions by the rotational position detection processing device 8a, the collimator 6 and the gamma ray detector 7 are moved or directed toward a different direction, and then the gamma ray data are measured again at a number of rotational positions by the rotational position detection processing device 8a. Thus, data necessary for visualization are collected from various positions and directions by moving the position of the collimator 6 and the gamma ray detector 7 or changing the measurement direction of the collimator 6 and the gamma ray detector 7. The collected data are imaged by the imaging calculation processing device 11, and the result of the visualization processing is displayed by the image display device 12.

Figure 6:
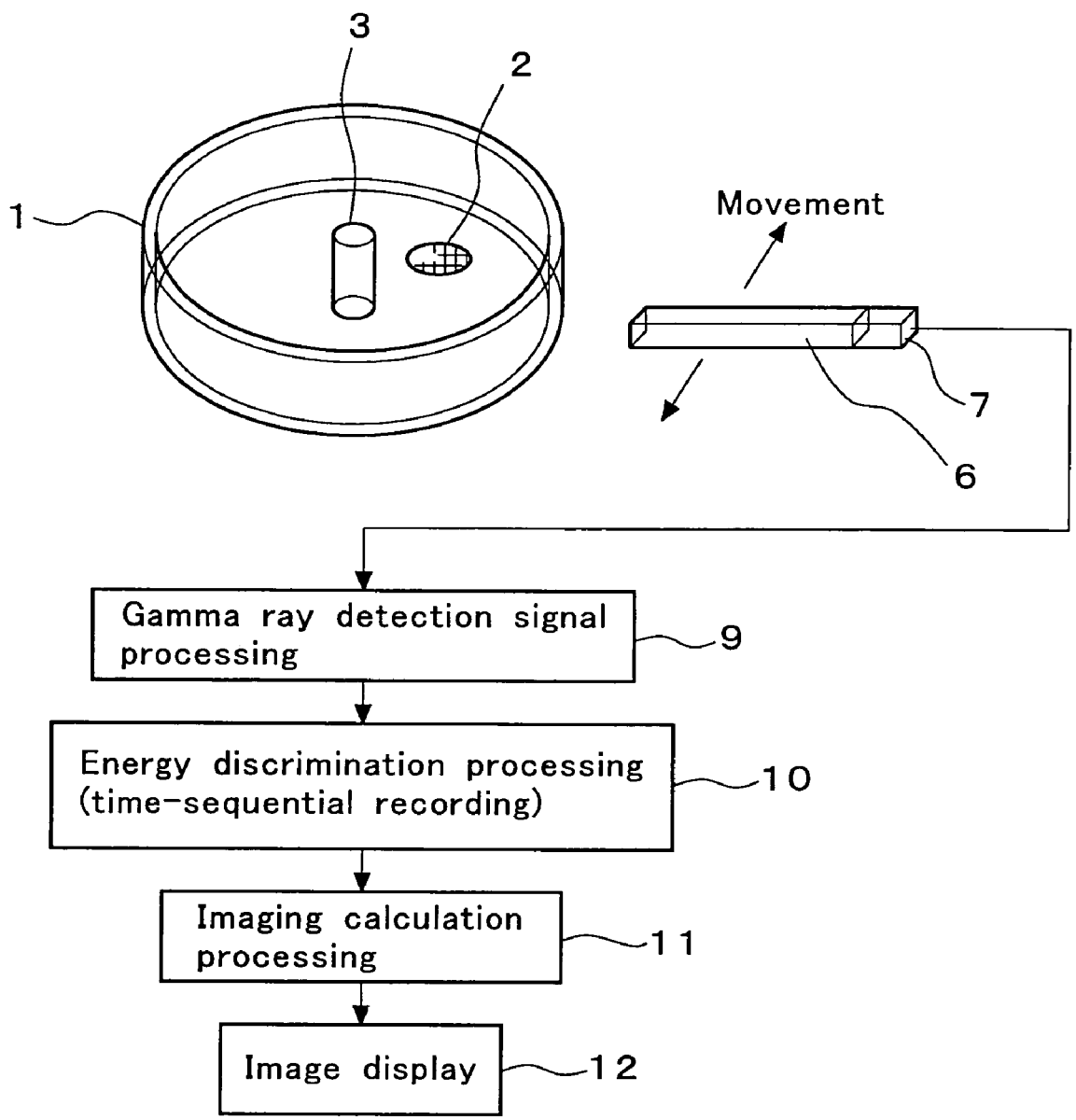
FIG. 6 is an illustration showing another embodiment of the visualizing apparatus according to the present invention.

FIG. 6 shows another embodiment of a visualizing apparatus utilizing a gamma ray source, according to the present invention, and also shows an example of visualization of the gamma ray source provided in a rotating body. A gamma ray source 2 is present in a container 1 and arranged to be rotatable about a rotating shaft 3. Here, the container 1 is formed to be cylindrical, but the shape and material of the container is not specifically restricted. Around the container 1, a collimator 6 and a gamma ray detector 7 are arranged so as to be time-sequentially moved, and the incoming direction and the energy of gamma rays can be detected by the collimator 6 and the gamma ray detector 7. The gamma rays emitted from the gamma ray source 2 are isotropically emitted and transmitted to the outside of the container 1, but the gamma rays in a certain incoming direction are made incident on the gamma ray detector 7 by the collimator 6.

The gamma rays incident on the gamma ray detector 7 are measured by a gamma ray detection signal processing device 9. The measured signal is discriminated by an energy discrimination processing device 10 in accordance with the energy, and is recorded together with the counted value. Then, the gamma ray detector 7 is moved and data necessary for imaging are collected. When the energy intensity is time-sequentially recorded at the time of measuring data, the size of the area where the radiation source is present and the measurement time of the data are related to each other, so that it is possible to obtain information about the size of the presence area in the direction of rotation. The data are used and imaged by an imaging calculation processing device 11, and the result of the visualization processing is displayed by an image display device 12. As a result, an image equivalent to that in the stationary state can be obtained.

Figure 7:
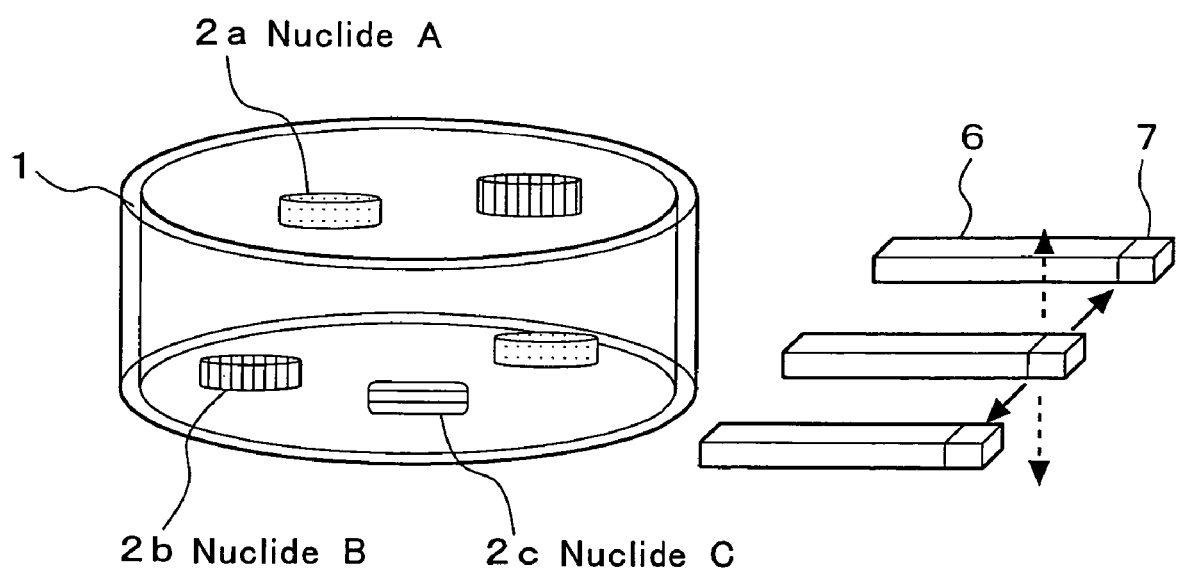
FIG. 7 is an illustration showing still another embodiment of the visualizing apparatus according to the present invention.

FIG. 7 shows, as still another embodiment according to the present invention, a case where nuclide discrimination of several kinds of gamma ray sources enclosed in a container 1 and three dimensional measurement of distribution state of the gamma ray sources, are performed. A collimator 6 and a gamma ray detector 7 are relatively moved in the vertical direction as well as in an oblique direction, so as to make data of gamma rays to different height directions collected. From the measurement data, information in accordance with the energy intensity can be obtained by an energy discrimination processing device, so that discrimination of the gamma ray sources and three-dimensional visualization of distribution state of the gamma ray sources can be effected.

Figure 8:
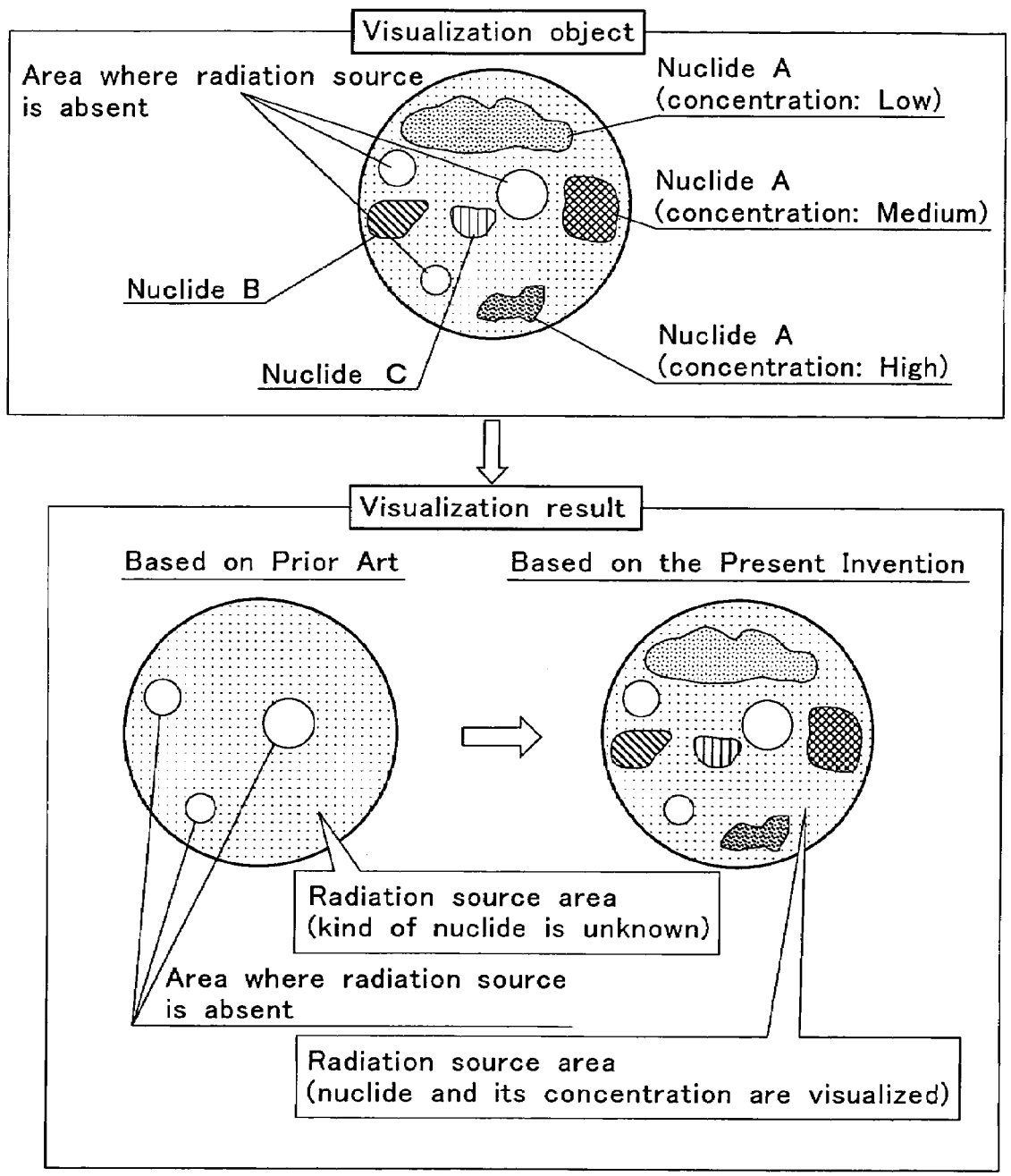
FIG. 8 is a conception figure for comparing the visualization based on the present invention with the visualization based on the prior art.

FIG. 8 is a conception figure showing a comparison between the present invention and the prior art (for example, Japanese Patent Laid-Open No. 2003-194740) in relation to the above described contents. As for the visualization result in the case where the visualization object which is the measurement object includes nuclide A (concentration: low), nuclide A (concentration: medium), nuclide A (concentration: high), nuclide B and nuclide C, only the presence or absence of the radiation source can be detected in the prior art, while in the present invention, the specification of radioactive nuclides and the visualization of concentration of radioactive nuclides can be effected for all of the nuclides to be visualized including nuclide A (concentration: low), nuclide A (concentration: medium), nuclide A (concentration: high), nuclide B, and nuclide C.

As a result, the present invention can be applied to discrimination of gamma ray sources and visualization of distribution state of gamma ray sources in a radioactive waste storage container, to discrimination of gamma ray sources and visualization of distribution state of gamma ray sources in a closed container with unknown contents enclosed therein. Further, the present invention can be applied to discrimination of gamma ray sources and visualization of distribution state of gamma ray sources during operation of the centrifugal separator, and can also be widely utilized for other fields.

What is claimed is:

1. A visualizing apparatus utilizing a gamma ray source, the apparatus comprising:
    a collimator which is arranged around a measurement object including a gamma ray source, and which permits gamma rays in a specific incoming direction from the gamma ray source to pass through the collimator;
    a gamma ray detector which performs a relative rotational movement or a relative linear movement together with the collimator with respect to the measurement object including the gamma ray source and which detects the gamma rays passing through the collimator;
    a gamma ray detection signal processing device which processes a gamma ray detection signal detected by the gamma ray detector to measure energy and counted value of the gamma rays;
    an energy discrimination processing device which performs discrimination and intensity analysis of radioactive nuclides by performing spectrum analysis of gamma ray energy and gamma ray intensity measured for each unit time or unit position;
    an imaging calculation processing device which forms images of concentration and space distribution of the gamma ray source in the measurement object for each discriminated radioactive nuclide; and
    an image display device which performs visual display based on calculation processing results from the imaging calculation processing device,
    wherein the energy discrimination processing device performs discrimination and intensity analysis of radioactive nuclides by taking into account position and time signals of the rotational movement or the linear movement; and
    wherein the imaging calculation processing device forms an image as an aggregation of discrete pixels by performing repetitive calculation of pixel values showing the gamma ray intensity, using a formula:

$$\lambda_j^{n+1} = \lambda_j^n \frac{\sum_{k=1}^{K} \frac{P_k^{n+1} \cdot c_{j,k}}{R_k^n}}{\sum_{k=1}^{K} c_{j,k}}$$

wherein:
    $\lambda_j$: j-th pixel value = gamma ray intensity;
    $P_k$: gamma ray energy and intensity data measured by the k-th gamma ray detector;
    $R_k$: data of gamma rays incident on the k-th detector based on the pixel value $\lambda^n_j$ after the n-th repetitive calculation;
    k: serial number indicating the position of the gamma ray detector (total K in the case of T directions);
    j: the j-th pixel;
    n: repeat count; and
    $C_{jk}$: probability that gamma rays emitted from the pixel j are detected at the k-th detector position (contribution rate to the pixel).

2. The visualizing apparatus of claim 1, wherein the gamma ray source is made of a liquid metal which is uniformly distributed in a cylindrical container having a diameter of about 1 m, a wall thickness of about 15 mm, a plurality of metal plates having a thickness of about 10mm, and a rotatable shaft.

3. The visualizing apparatus of claim 2, further comprising a rotational position detection marker provided on an outer circumference of the container and a rotational position detecting sensor for detecting a rotational position of the container provided outside of the container.

4. The visualizing apparatus of claim 3, wherein the rotational position detecting sensor is one selected from the group consisting of optical, magnetic, and contact, and the rotational position detecting sensor is capable of responding to and detecting the rotational position detection marker.

* * * * *